(12) United States Patent
Bacher et al.

(10) Patent No.: US 8,398,618 B2
(45) Date of Patent: Mar. 19, 2013

(54) MEDICAL INSTRUMENT WITH A DETENT

(75) Inventors: Uwe Bacher, Tuttlingen (DE); Sabine Summerer, Ebersberg (DE); Sebastian Frey, Waghaeusel (DE)

(73) Assignee: Karl Storz GmbH & Co. KG (DE)

(*) Notice: Subject to any disclaimer, the term of this patent is extended or adjusted under 35 U.S.C. 154(b) by 1023 days.

(21) Appl. No.: 12/415,182

(22) Filed: Mar. 31, 2009

(65) Prior Publication Data
US 2009/0247995 A1   Oct. 1, 2009

(30) Foreign Application Priority Data
Mar. 31, 2008 (DE) .......... 10 2008 017 299

(51) Int. Cl.
*A61B 17/00* (2006.01)
(52) U.S. Cl. .................. 606/1; 606/205
(58) Field of Classification Search .......... 600/131, 600/139–152; 606/51–53, 113–114, 139–148, 606/205–213; 604/61, 95.01–95.05, 523, 604/528; 227/175.1, 175.2, 175.3, 175.4, 227/176.1, 178.1, 180.1
See application file for complete search history.

(56) References Cited

U.S. PATENT DOCUMENTS

| | | | | | |
|---|---|---|---|---|---|
| 823,155 | A | * | 6/1906 | Booker | 81/338 |
| 4,483,562 | A | * | 11/1984 | Schoolman | 294/104 |
| 4,722,339 | A | * | 2/1988 | Dreier et al. | 606/208 |
| 5,282,800 | A | * | 2/1994 | Foshee et al. | 606/52 |
| 5,293,878 | A | * | 3/1994 | Bales et al. | 600/564 |
| 5,334,198 | A | * | 8/1994 | Hart et al. | 606/52 |
| 5,370,659 | A | * | 12/1994 | Sakashita | 606/205 |
| 5,601,601 | A | * | 2/1997 | Tal et al. | 606/207 |
| 5,603,723 | A | * | 2/1997 | Aranyi et al. | 606/205 |
| 5,618,294 | A | | 4/1997 | Aust et al. | |
| 5,626,608 | A | | 5/1997 | Cuny et al. | |
| 5,827,323 | A | | 10/1998 | Klieman et al. | |
| 6,077,287 | A | | 6/2000 | Taylor et al. | |
| 2006/0026784 | A1 | * | 2/2006 | Moskovich et al. | 15/110 |
| 2006/0206144 | A1 | | 9/2006 | Miersch | |
| 2007/0038230 | A1 | | 2/2007 | Stone et al. | |
| 2007/0299469 | A1 | | 12/2007 | Carpenter et al. | |

FOREIGN PATENT DOCUMENTS

| | | |
|---|---|---|
| CH | 667584 A5 | 10/1988 |
| DE | 69203964 T2 | 4/1996 |
| DE | 10232086 A1 | 1/2004 |
| DE | 10353552 A1 | 6/2005 |
| DE | 202005020964 U1 | 1/2007 |
| WO | 2006071120 A1 | 7/2006 |

OTHER PUBLICATIONS http://dictionary.reference.com/browse/clip, retrieved Jul. 29, 2012.*
Catalogue of Karl Storz, Die Welt Der Endoskopie, Laparoskpie, 5th Edition Jan. 2005 (2 pages).
European Search Report; EP 09 15 6432; Jul. 17, 2009; 5 pages.

* cited by examiner

*Primary Examiner* — Ryan Severson
*Assistant Examiner* — David Eastwood
(74) *Attorney, Agent, or Firm* — St. Onge Steward Johnston & Reens, LLC

(57) ABSTRACT

A medical instrument comprises a shaft which is connected at the proximal end to a handle, and it also comprises an insert which is guided along the shaft and which is connected at the proximal end to a movable grip part of the handle. At its distal end, the insert has a tool which can be actuated by pivoting of the grip part. A lock is also provided which can be brought into locking engagement with the movable grip part. To cancel the lock function, a detent is provided which can be brought between lock and movable grip part, such that the lock function can be cancelled by the detent.

19 Claims, 11 Drawing Sheets

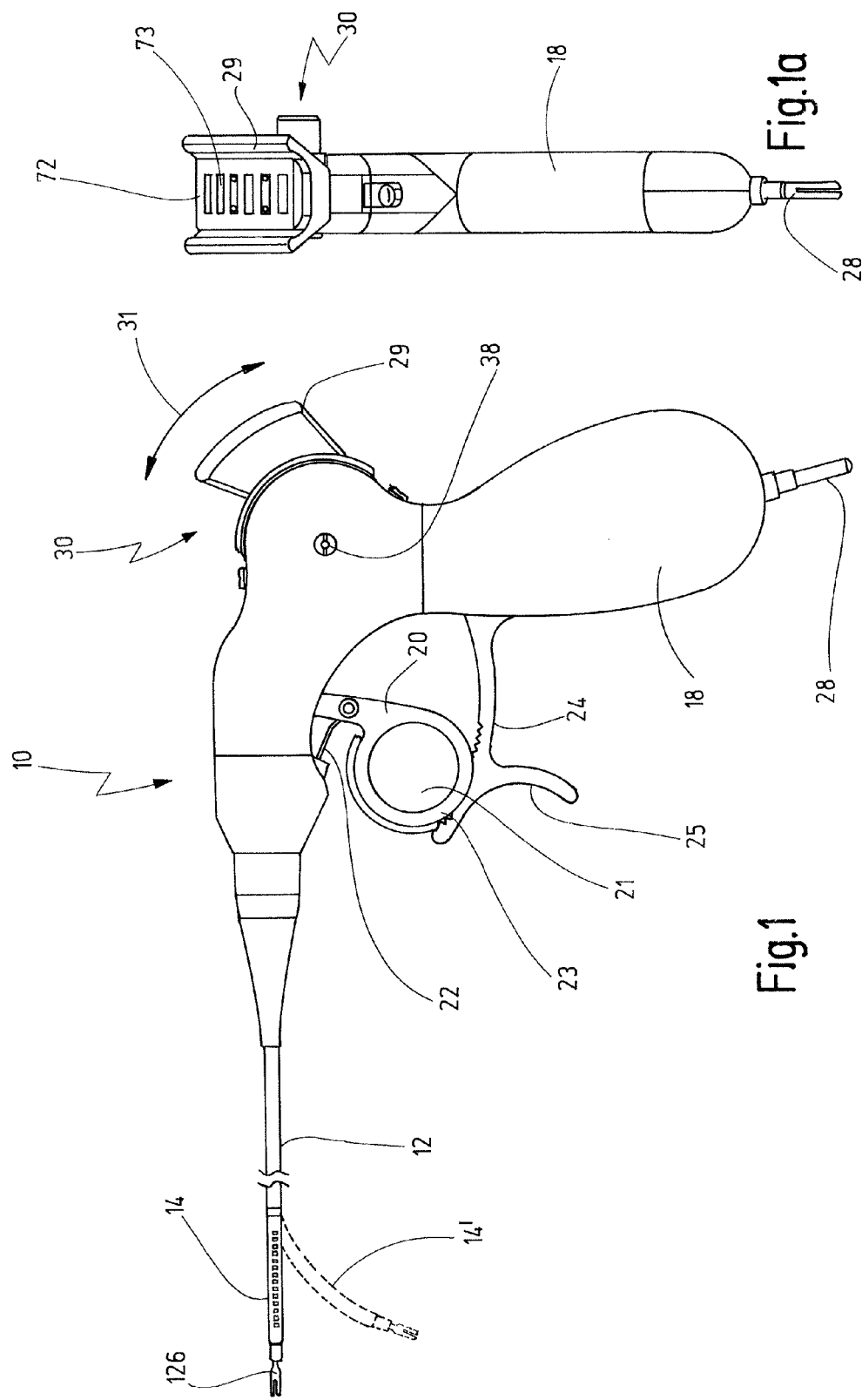

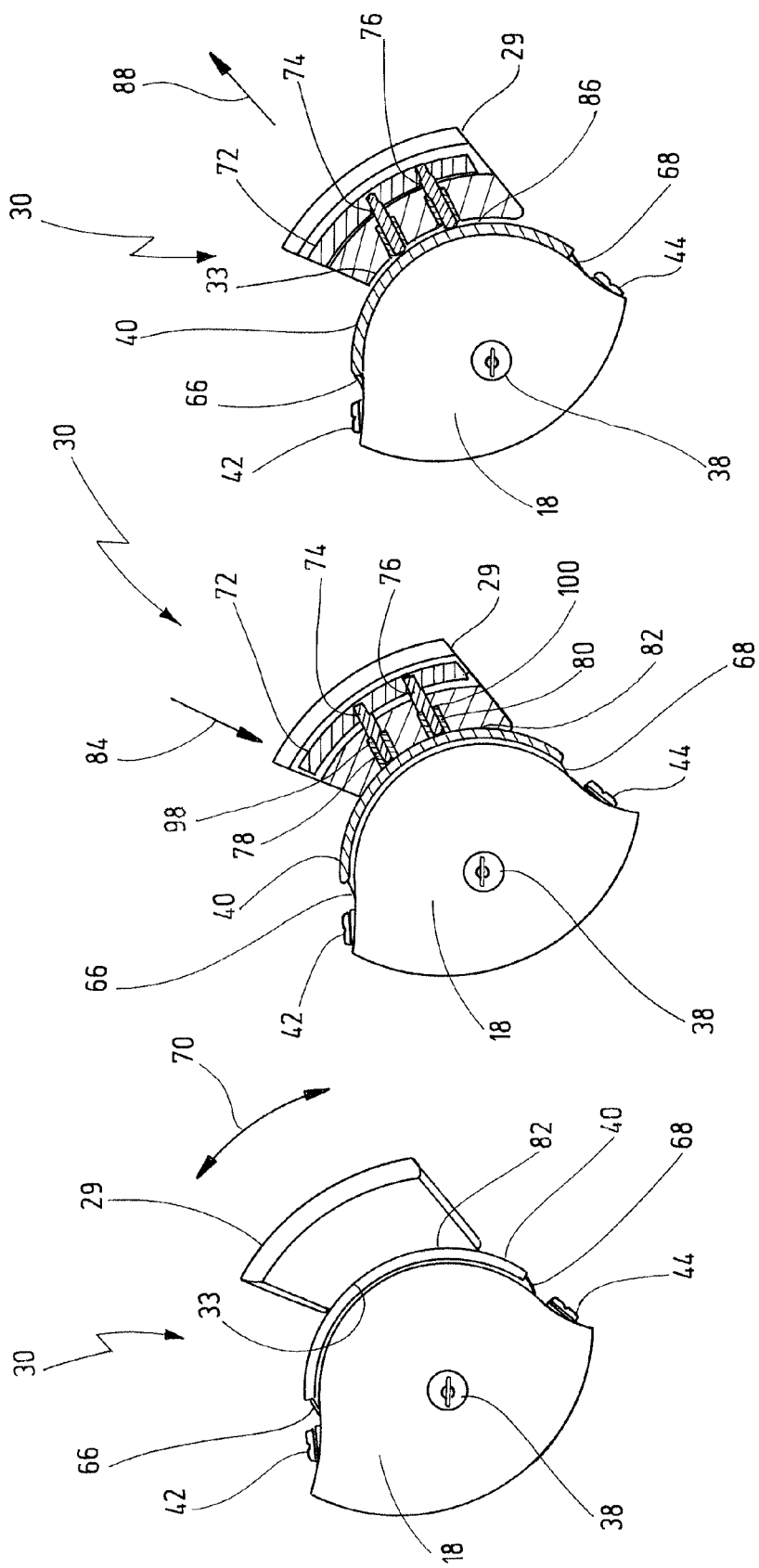

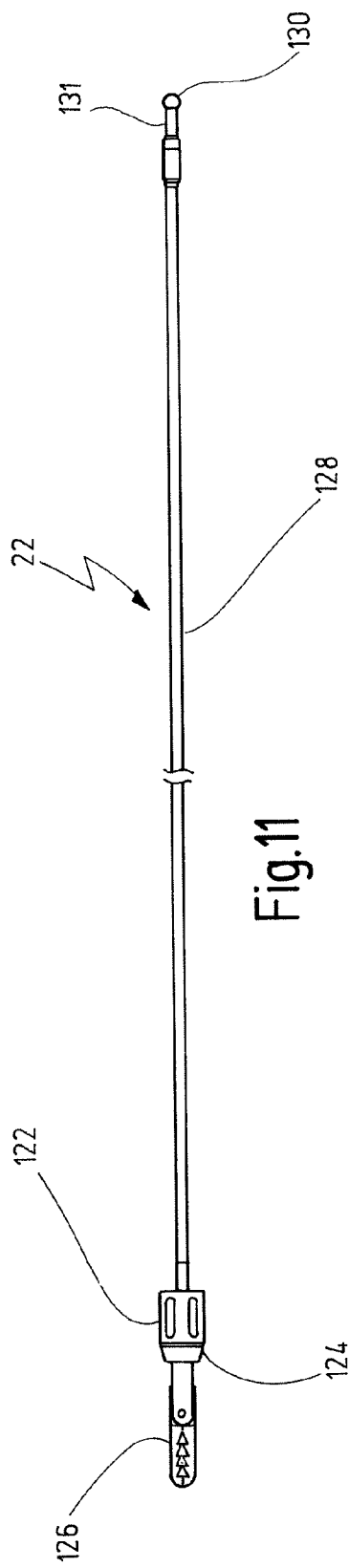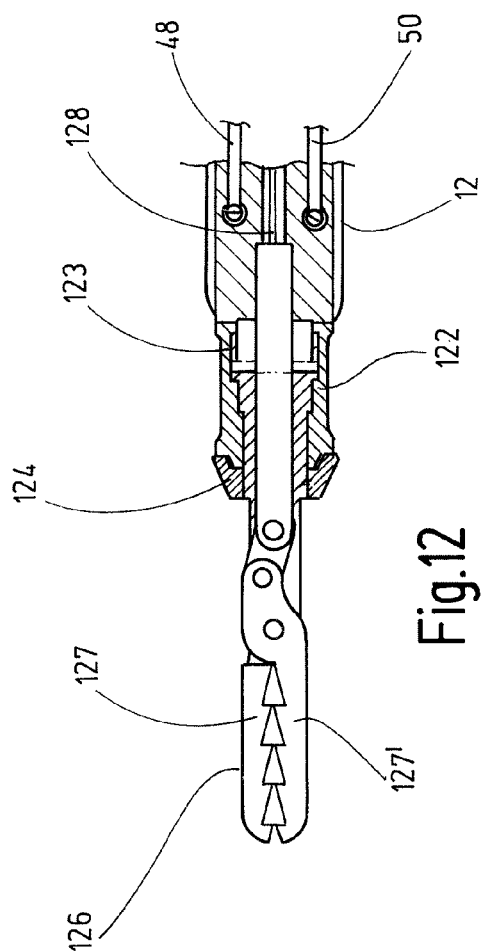
Fig.11
Fig.12

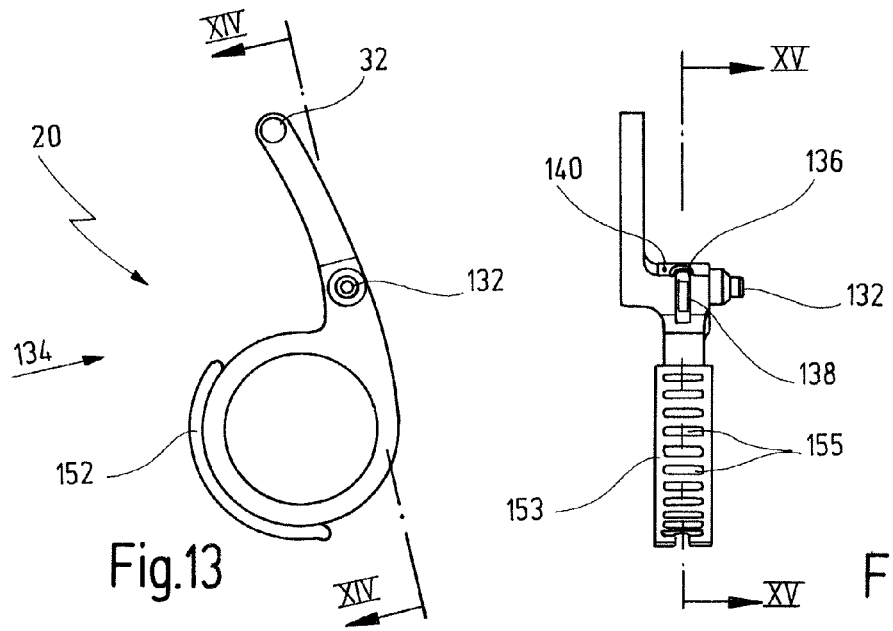
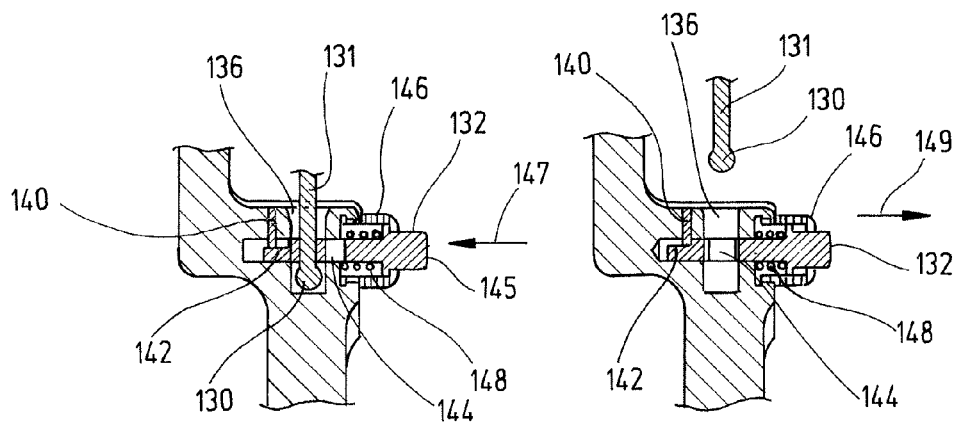
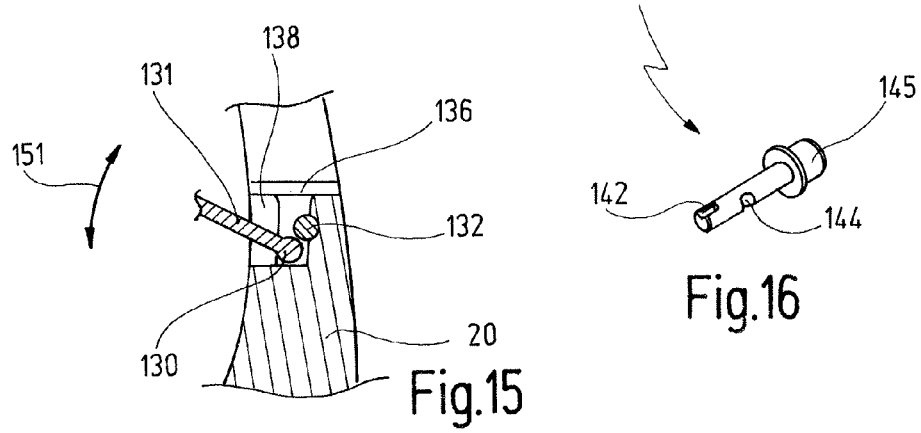

MEDICAL INSTRUMENT WITH A DETENT

BACKGROUND OF THE INVENTION

The invention relates to a medical instrument with a shaft which is connected at the proximal end to a handle, with an insert which can be guided along the shaft and which is connected at the proximal end to a movable grip part of the handle and at its distal end has a tool which can be actuated by pivoting of the grip part, and with a lock which can be brought into locking engagement with the movable grip part.

A medical instrument of this kind in the form of dissecting forceps or gripping forceps is known from page 77 of section 4 "Dissecting forceps and gripping forceps" of the catalogue of the firm Karl Storz GmbH & Co. KG, Tuttlingen, Germany "Laparoskopie", 5th edition January 2005.

The movable grip part, which actuates the tool, can be fixed by means of the lock. The lock is in most cases composed of a rod-shaped grip part, which is mounted on a handle, in most cases at an immovable grip part. On the side directed towards the movable grip part, the lock has teeth that engage with a locking pin on the movable grip part.

In some designs, the inclination of the flank of the teeth is such that the movable grip part can run over the teeth in one direction, while a movement in the opposite direction is blocked.

A common practical use is that of gripping forceps in which, after a section of tissue has been gripped, the movable grip part is locked by means of the lock, such that the jaw parts are held in a defined position. In some designs however, as has already been mentioned, it is possible to move the movable grip part in one direction, mostly into the closing position of the jaw parts, such that the secured tissue is held still more firmly than before. However, a movement in the opposite direction, i.e. further opening of the jaw parts, is blocked by the lock. This ensures that a tissue that has been gripped is no longer released, such that the operator is able to concentrate on other procedures that he might wish to perform with the forceps, for example coagulation or the like.

Should the operator wish to release the lock, he has to move the latter away from the grip part, and only then is he able to move the movable grip part in both directions again. However, since the lever-type lock is often pretensioned by a spring force, the operator has to hold the lock permanently away if he wishes to move the second grip part freely back and forth.

This is ergonomically disadvantageous and occupies at least one finger of the hand, which finger has to press the lock permanently away.

In medical instruments with a bendable shaft, a further control element is provided on the instrument, namely the control element via which the shaft is bent.

In some designs, particularly in dissecting forceps, it is desirable for the movable grip part to be fixed via a lock in some manoeuvres, while in other manoeuvres, for example cutting, it is desirable for it to be movable freely in both directions. Since, in the case of an instrument with a bendable shaft, dissecting work is also intended to be performed with the shaft bent, the operator has to be able to manoeuvre several adjusting elements and be able to control their locking or release.

Since medical instruments of this kind are mostly used in minimally invasive surgery, the field of view of the operator at the distal end is in any case limited and he has to view this area either through an endoscope or on a monitor arranged alongside, and it is therefore very important that he is able to achieve the various control states using the fingers of the hand with which he has taken hold of the medical instrument, and that he is able to do so in a manner that is as ergonomic as possible.

It is therefore object of the present invention to develop a medical instrument, particularly one with a bendable shaft, in such a way that more operationally reliable and ergonomic handling is possible, in particular as regards the locking and unlocking of the movable grip part.

SUMMARY OF THE INVENTION

This object is achieved by a medical instrument comprising a shaft, a handle connected to a proximal end of said shaft, an insert guided along said shaft, said insert being connected at a proximal end thereof to a movable grip part of said handle, and having a tool at a distal end, said tool being actuated by said movable grip part, and a lock which can be brought into a locking engagement with said movable grip part, wherein a detent is provided, said detent can be brought between said lock and said movable grip part, thereby cancelling a lock function of said lock by said detent.

This measure has the advantage that, if the operator wishes to cancel the lock function for a certain period of time or permanently, he simply brings the detent between the lock and the grip part, such that he is then able to freely perform the required movements with the movable grip part, for example to perform a dissecting procedure using a reciprocating movement, for example for cutting tissue by opening and closing of jaw parts.

The operator now no longer has to take the trouble to move the lock away from its engagement with the movable grip part and hold it there, since, according to the invention, this is achieved by the detent being brought between the lock and the movable grip part. After the operator has brought the detent between the lock and the movable grip part, he also need not worry that the locking function could start again. This would be very inconvenient, for example if he intends to make a very complicated incision, or an incision on a vital organ, for example the heart, since this incision would suddenly be abruptly stopped by an unwanted locking movement.

Thus, this lock function can be cancelled in a very safe way, and it is also done ergonomically since only a single manipulation is needed, namely that of bringing the detent between the lock and the movable grip part.

In a further embodiment of the invention, the detent can be brought from a first position, in which the lock function is activated, to a second position, in which the lock function is deactivated.

This measure has the advantage that the operator does not have to concentrate too much on switching the detent between a defined first position, in which the lock function is activated, and the second position, in which the lock function is deactivated. The same applies to the reverse procedure.

In a further embodiment of the invention, the detent can be held in the first position.

In a further embodiment, the detent can also be held in the second position.

These measures have the advantage that, for operational safety, the detent is held in these two positions, such that no unwanted release takes place and the detent does not move to another position.

In a further embodiment of the invention, the detent is guided in a guide.

This measure has the advantage that the switching of the detent between the two positions is guided by the guide and can thus be done safely and ergonomically. Ergonomically, that is, because the operator does not have to pay attention to the path of movement, since this is ensured by the guide, and attention simply has to be applied to bringing the detent from the one position to the other.

In a further embodiment of the invention, the guide has at least one groove in which a projecting element of the detent engages.

This measure has the advantage that the guide is technically very easy to produce and ensures a reliable guide function.

In a further embodiment of the invention, the detent is rounded in the area in which it comes into contact with teeth of the lock.

This measure has the advantage that the detent can slide relatively gently across the teeth and can be moved or brought between the movable grip part and the teeth of the lock. This also ensures that the teeth are not damaged, such that, when the lock function is again desired, they can reliably ensure this function.

In a further embodiment of the invention, the detent is mounted on the movable grip part.

This measure has the advantage, in ergonomic terms, that the detent can be brought to the two positions using, for example, the finger which holds or moves the grip part.

In a further embodiment of the invention, the detent is mounted displaceably on the grip part and can be displaced there between the first and second positions.

This measure, as has already been stated, has the advantage in ergonomic terms that the lock can be moved to the different positions by a simple displacement of the grip part.

In a further embodiment of the invention, the grip part has a finger opening on whose outer ring section the detent is mounted.

This measure has the advantage that the detent can be displaced, either by the finger inserted in the ring section or by the next again finger, along the outer face of the ring section of the finger opening.

This can be done in a functionally reliable and ergonomic manner.

In a further embodiment of the invention, the detent is designed as a curved element whose curvature is adapted to the ring section of the grip part.

This permits a particularly ergonomic displacement of the detent along the outer face of the ring section of the grip part.

In a further embodiment of the invention, the curved element has features that increase its grip.

These features have the advantage that the operator, even without looking, feels that he is now touching the detent, and at the same time, the improved degree of grip ensures that the operator's finger does not slip from the detent during the displacement.

In a further embodiment of the invention, the features are chosen from elevations, flutings, recesses, punches and hollows.

This measure has the advantage that these features, on the one hand, are technically very easy to produce and, on the other hand, provide a very good degree of grip for the operator.

In a further embodiment of the invention, guide pins project from the detent and engage in each case in a groove on the sides of the ring section.

This measure has the advantage of ensuring a reliable guiding of the detent on the ring section.

In a further embodiment, the detent has lateral covers that engage laterally over the ring section.

This measure has the advantage that the guide is concealed by the covers and, therefore, cannot be touched by the operator's finger. The aforementioned guide pins can also be held by the cover.

In a further embodiment of the invention, the detent extends along the outer face of the ring section.

This measure has the advantage of creating what is an ergonomically very favourable position for the detent, which can be found very easily with a finger, such that the operator is able to actuate the detent without particularly concentrating on this. The fact that the detent is arranged along the outer face of the ring section affords the possibility of leaving in place the finger inserted into the inner opening of the ring section and of controlling the detent with another finger. Alternatively, the finger placed in the ring section can first be taken out and the detent then moved specifically by this finger.

In a further embodiment of the invention, clip elements are arranged on the detent and enter into connection with retaining pins in the first and second positions, respectively.

This measure has the advantage that the detent is retained in both positions by very simple elements and, for the operator, the clipping action is also easy to detect by touch, since the operator senses the clip elements engage.

In a further embodiment of the invention, one clip element, in the second position, enters into a retaining connection with the locking pin that engages with the lock.

This has the advantage that this locking pin performs a dual function, firstly as a retaining pin for the detent and secondly as a locking element for the teeth of the lock. In addition, this measure ensures in a particularly simple way that this locking pin can no longer come into contact with the lock, since it is now covered by the clip element of the detent.

In a further embodiment of the invention, the clip elements are arranged in a step engaging in a circumferential groove that is cut out in the movable grip part.

This measure has the advantage that these clip elements, covered by the detent, are received in the outer circumferential area of the grip part and are thus also protected there against contamination and the like, thereby ensuring a functionally reliable design.

In a further embodiment of the invention, the lock is designed as a pivotable lever which is pretensioned in the direction of the movable grip part and which is articulated on the handle.

This measure has the advantage that, if the lock function is wanted, the latter re-establishes itself independently when the detent is moved out from the position between the grip part and the lock. The pretensioning has the effect that the lock and its teeth are pressed onto the movable grip part, such that the locking action again takes place there with the corresponding locking feature, for example with the aforementioned locking pin.

In a further embodiment of the invention, the lock has an attachment via which the lock can be withdrawn from the movable grip part.

This measure has the advantage that the lock, which is in most cases designed as a rod or ridge-like structure, can be easily withdrawn from the movable grip part via the attachment.

This allows the operator to briefly cancel the lock function, for example so as to quickly execute a movement in just one direction, and then to immediately activate the lock function again without having to push in the detent.

In a further embodiment of the invention, the attachment is arc-shaped and can receive a finger of the hand that has taken hold of the handle.

This measure has the particular advantage, in ergonomic terms, that this movement too can be effected safely and easily.

It will be appreciated that the aforementioned features and the features still to be explained below can be used not only in the respectively cited combination but also in other combinations or singly, without departing from the scope of the present invention.

BRIEF DESCRIPTION OF THE DRAWINGS

The invention is described and explained in more detail below on the basis of a number of selected illustrative embodiments and with reference to the attached drawings, in which:

FIG. 1 shows a side view of a medical instrument with a bendable shaft,

FIG. 1a shows the medical instrument of FIG. 1 from the proximal direction, i.e. as seen by the operating surgeon, FIG. 4 shows a partial detail of the handle to illustrate the locking of a bend control mechanism, FIG. 4a shows the detail from FIG. 4, with a sectional view through a control element of the bend control mechanism in the locked state, FIG. 5 shows the detail as in FIG. 4a, in the state when not locked, FIG. 11 shows a side view of a tool insert for the medical instrument in FIG. 1, FIG. 12 shows an enlarged detail view of the distal end of the tool in FIG. 11, FIG. 13 shows a side view of a grip part of the instrument shown in FIG. 1, FIG. 13a shows a view of the grip part seen from the direction of the arrow 134 in FIG. 13, FIG. 14 shows an enlarged partial cross section along the line XIV-XIV in FIG. 13, with the end of the tool insert from FIG. 11 in the locked state, FIG. 14a shows a view corresponding to FIG. 14, with the end of the tool insert released, FIG. 15 shows an enlarged partial cross section along the line XV-XV in FIG. 13a, with the end of the tool insert from FIG. 11 engaged, FIG. 16 shows a perspective view of a catch on its own.

DETAILED DESCRIPTION OF A PREFERRED EMBODIMENT

Figure 1B:
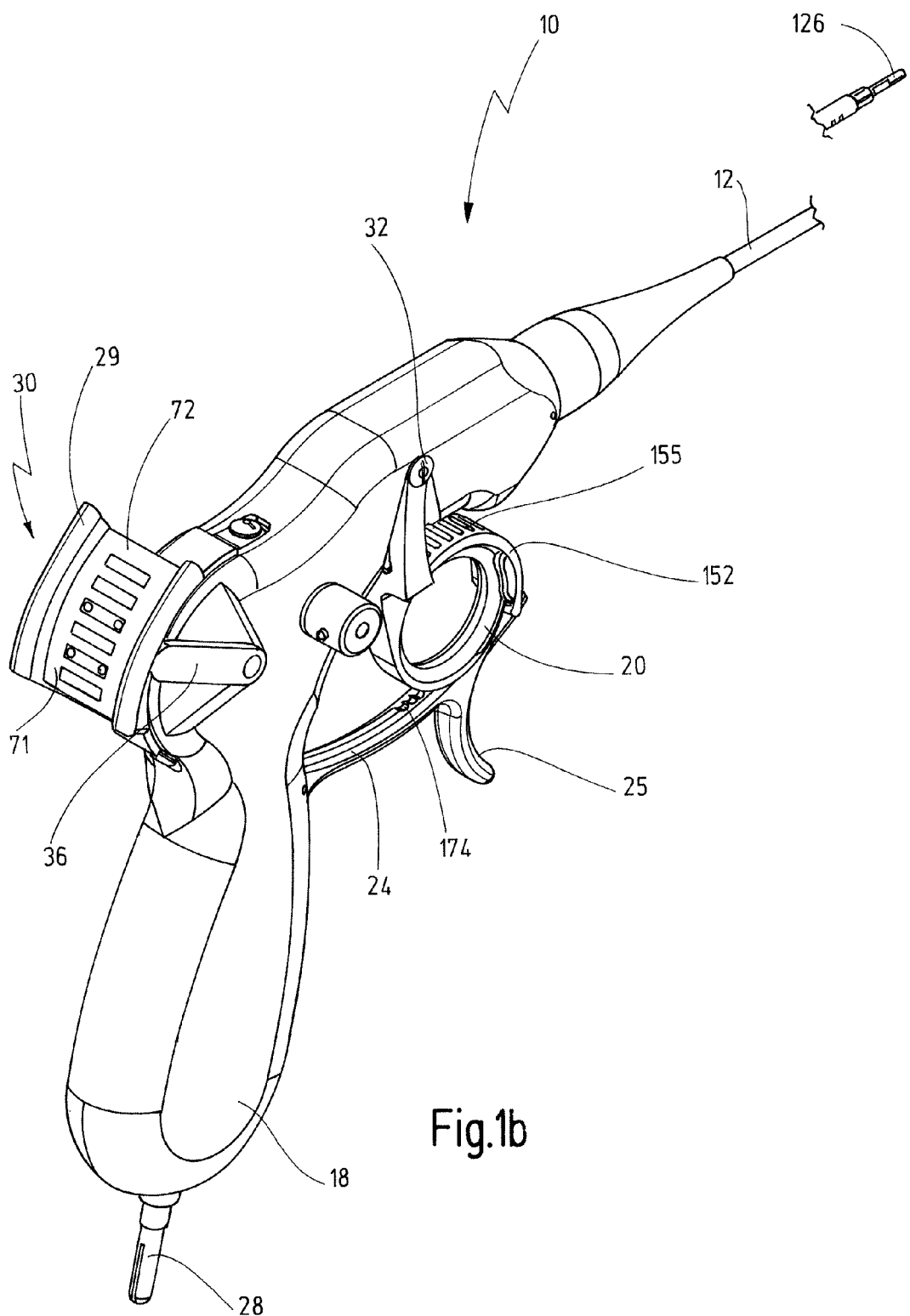
FIG. 1b shows a perspective view of the medical instrument.

A medical instrument as shown in the figures is designated in its entirety by reference sign 10.

The medical instrument 10 shown in FIG. 1 comprises a flexible shaft 12 which has a bendable area 14 at its distal end. A tool 126 is arranged distally on the area 14. The tool 126 constitutes a distal end of an insert 22 shown in FIG. 11. The proximal end of the shaft 12 is connected to a handle 18.

The handle 18 in turn comprises a movable grip part 20. The latter has a round opening 21 which is delimited by a ring portion 23 and through which preferably the index finger of the operating surgeon can be guided in order to execute a movement of the grip part 20, which is pivotable about the pivot axis 32 shown in FIG. 2. The grip part 20 is connected to the proximal end of the insert 22. By virtue of the connection of the grip part 20 to the insert 22, it is operatively connected to the tool 126 and thus serves to actuate the latter, e.g. to open and close a jaw part.

Moreover, the grip part 20 can be brought into contact with a lock 24 that can prevent unwanted movement of the grip part 20 in a distal direction. To permit a release of the lock connection, the lock 24 has, among other things, an arc-shaped attachment 25 which permits a pivoting movement of the lock 24 by the operating surgeon, preferably with the middle finger, as is described in connection with FIG. 17 et seq.

Moreover, the handle 18 is provided with a control element 29 of a bend control mechanism 30, the movement of which in the directions of the double arrow 31 about a pivot axis 38, running perpendicular to the illustrated axis of the shaft 12, permits control of the bending of the bendable end 14 of the shaft 12. An example of the direction of bending is indicated in FIG. 1 by the angled end 14'.

FIG. 1a is a view looking at the control element 29 of the bend control mechanism 30 and at an actuating element 71 in the form of a trigger 72 located thereon. The trigger 72 can be actuated by a thumb of the operating surgeon, as a result of which a movement of the control element 29 is permitted. To provide better grip, grooves 73 are arranged for this purpose on the trigger 72.

The instrument 10 also has a current attachment 28, which can be used, for example, to supply current to optional coagulation inserts.

Figure 2:
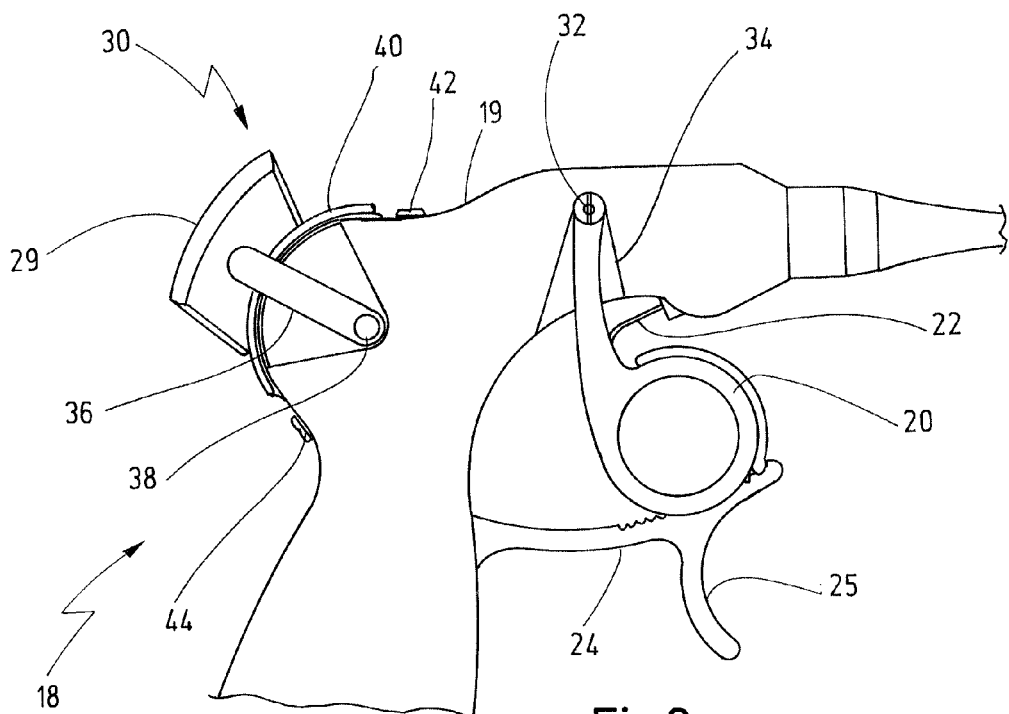
FIG. 2 shows a partial side view of the medical instrument of FIG. 1, from the opposite side.

FIG. 2 indicates the range of pivotability of the grip part 20 about the pivot axis 32 in the area of a recess 34. The control element 29 is connected to the pivot axis 38 via a connecting arm 36.

Between a housing 19 of the handle 18 and the control element 29, there is a friction element in the form of a friction plate 40, which is fastened to the outer face of the handle 18 by screws 42 and 44. As will be described in more detail below, this friction plate 40 is used to stop the bend control mechanism 30 in a defined position.

Figure 3:
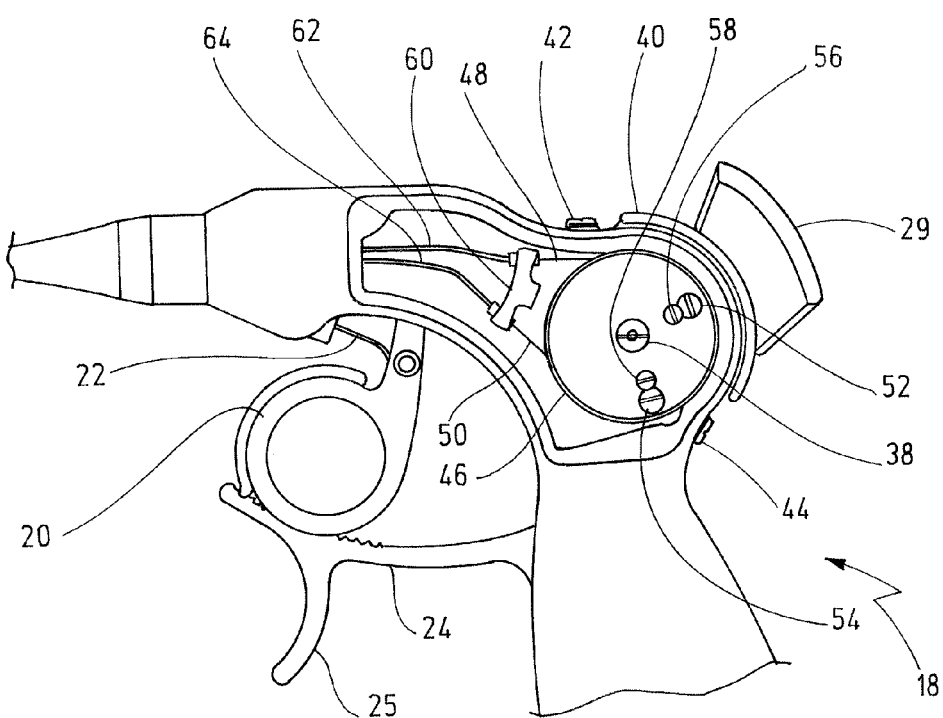
FIG. 3 shows a partial side view of the medical instrument of FIG. 1, with the housing of the handle opened.

A drum 46 shown in FIG. 3 is secured on the pivot axis 38 and is thus operatively connected to the control element 29 of the bend control mechanism 30 via the connecting arm 36. A corresponding actuation of the control element 29 thus also results in movement being transferred directly to the drum 46. Two control wires 48 and 50 extending through the shaft 12 from the bendable end 14 of the shaft 12 end on the drum 46, said wires 48 and 50 each extending to the sides of the pivot axis 38 and, in this illustrative embodiment, being fastened on the drum by fastening screws 52 and 54 in combination with securing screws 56 and 58. For this purpose, the control wires 48 and 50, emerging proximally from sleeves 62 and 64, are conveyed through a guide 60 to the drum 46. The control wires 48 and 50 are the actuating elements for the bendable end 14. Together with the drum 46 and the connecting arm 36, they thus provide the operative connection between the control element 29 of the bend control mechanism 30 and the bendable end 14. A more detailed description of their function is given later in connection with FIG. 9.

The feature whereby the bend control mechanism 30, and thus the bendable end 14 of the shaft 12, can be locked with the aid of the friction plate 40 will now be described in detail in connection with FIGS. 4 to 8.

FIG. 4 shows that an underside 33 of the control element 29 is in direct contact with the friction plate 40, which is fastened on the handle 18 via angled spring plates 66 and 68 and by means of the screws 42 and 44. The friction plate 40 thus extends at a spacing from the outside of the handle 18 on which it is mounted. A movement of the control element 29 about the pivot axis 38 in the directions of the double arrow 70 is avoided or braked by the frictional contact between the control element 29 and the friction plate 40 on a friction contact face 82.

FIG. 4a shows that the bend control mechanism 30 comprises the trigger 72. The latter, as can also be seen in FIG. 1b, is easily accessible to the operating surgeon from the proximal direction. Protruding from the trigger 72 are pins 74, 74', 76, 76' (see also FIG. 7) which at the distal end are guided through and held by sleeves 78, 80 in the body of the control element 29. The tips of the pins bear directly on the friction plate 40 and thus provide an operative connection between the trigger 72 and the friction plate 40. By pressing the trigger 72 in the direction of the arrow 84, the pins are moved axially through bores 98, 100 in the body of the control element 29, and they thus press the friction plate 40 in the direction of the handle 18. The friction plate 40 thus moves away from the underside 33 of the control element 29. The friction contact face 82 is thus freed and a gap 86 is formed, as is shown in FIG. 5. The flexibility needed for this change of position of the friction plate 40 is permitted principally by the spring plates 66 and 68, but also by elongate openings 102 and 104, as are shown in FIG. 8.

The position resulting from the actuation of the trigger 72, as shown in FIG. 5, now permits a low-friction movement of the control element 29, as is shown by the double arrow 70 in FIG. 4.

Only the tips of the four pins 74, 74', 76, 76' rest on the friction plate 40 and slide with low friction across the surface thereof. For this purpose, they can be made of a low-friction plastic material, for example. It is also possible for a metal main body to be covered by the low-friction material, or for a low-friction tip to be fitted onto a metal stump.

When the operating surgeon now takes his finger, preferably the thumb, off the trigger 72, the tension afforded by the spring plates 66 and 68 means that the friction plate 40 is pressed back against the underside 33 of the control element 29 of the bend control mechanism 30, such that the gap 86 disappears and the friction contact face 82 is once again present. Correspondingly, the pins 74, 74', 76, 76' and thus the trigger 72 also undergo a proximal movement in the direction of the arrow 88. In this way, the bend control mechanism 30 is locked in its position again. This can therefore be done steplessly within the pivot range of the control element 29.

Figure 6:
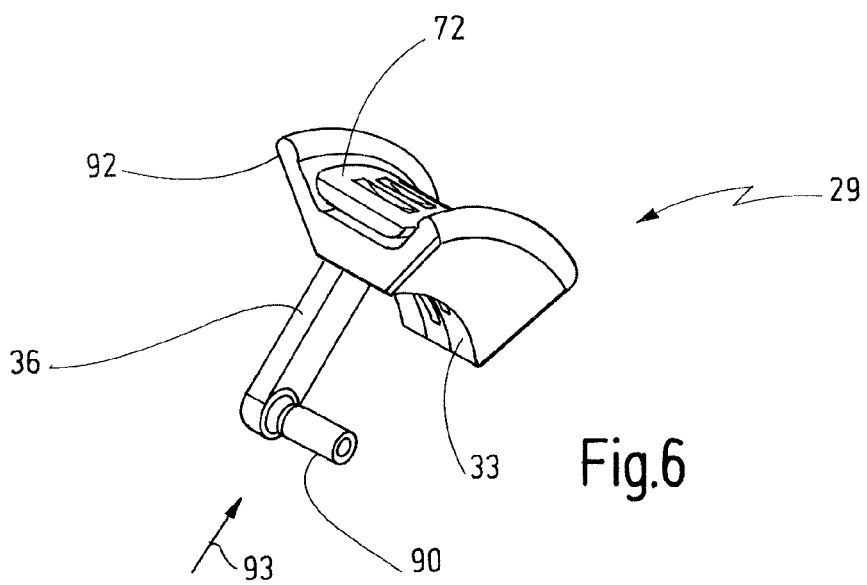
FIG. 6 shows the control element of the bend control mechanism in a perspective view on its own.
Figure 6A:
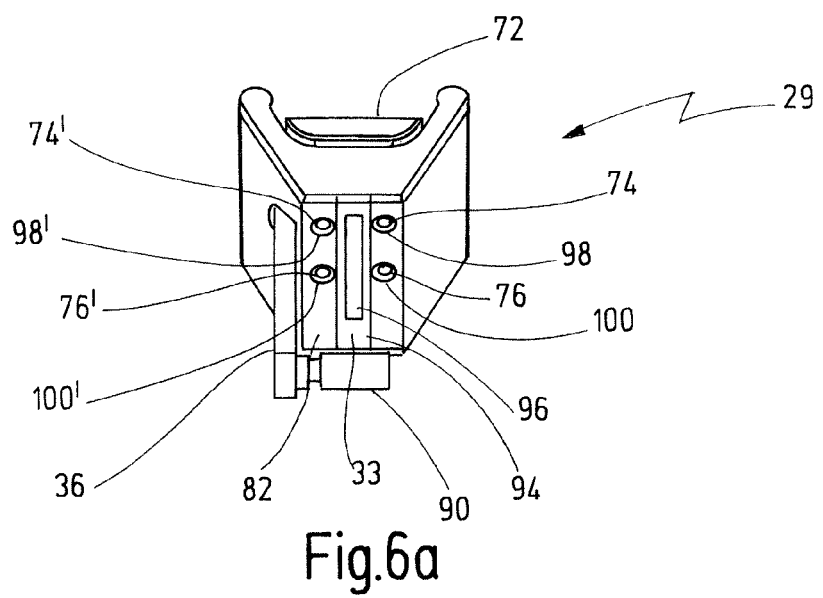
FIG. 6a shows a view of the control element from FIG. 6 along the arrow 93 in FIG. 6.
Figure 7:
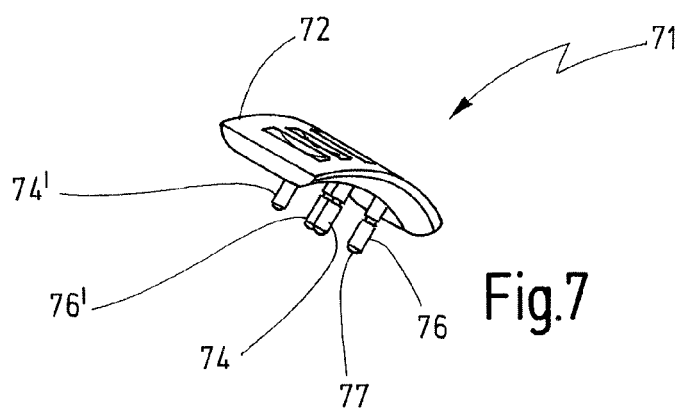
FIG. 7 shows an actuating element of the bend control mechanism in a perspective view on its own.
Figure 8:
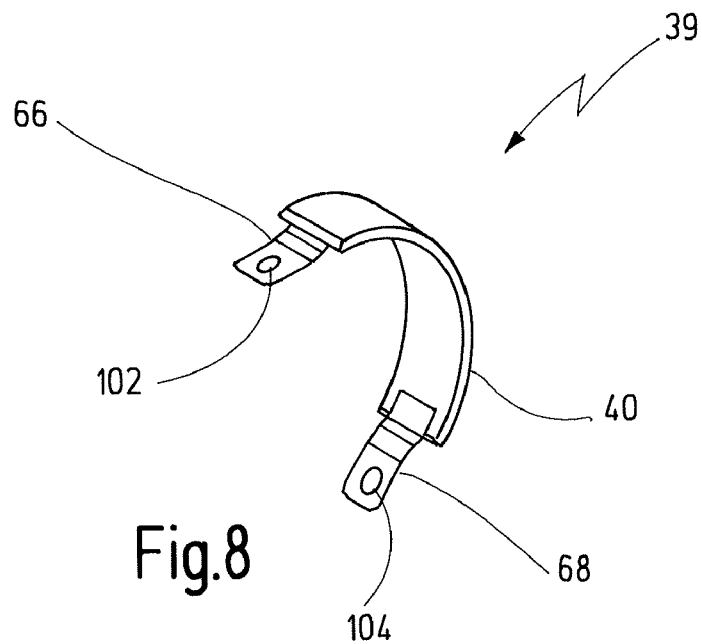
FIG. 8 shows a perspective view of a friction element for locking the bend control mechanism.

The control element 29 of the bend control mechanism 30 is shown in more detail in FIGS. 6, 6a and 7, in which the trigger 72 and the proximal access to the latter can be clearly seen. The trigger 72 is fastened on a finger-receiving part 92 which is mounted on the pivot axis 38 via the connecting arm 36 and with a pin 90.

FIG. 6a shows the underside 33 which comes into contact with the friction plate 40. In this illustrative embodiment, the trigger 72 is equipped with four pins 74, 74', 76 and 76', which extend axially and are movable within the bores 98, 98', 100 and 100'. Arranged between the two pairs of pins 74, 76 and 74', 76', there is a plastic inlet piece 96 which is fastened on the finger-receiving part 92 by a retaining plate 94. This plastic inlet piece 96 serves to increase the friction between the control element 29 and the friction plate 40 and, thereby, reinforce the locking in the desired position.

The trigger 72 with the four pins 74, 74', 76 and 76' can be seen clearly in FIG. 7. By virtue of their distally rounded tips 77, the friction as they slide on the friction plate 40 is reduced to a minimum, which facilitates the use of the bend control mechanism 30.

The illustrative embodiment of the friction element 39 with the friction plate 40 shown in FIG. 8 is connected at the opposite ends to the angled spring plates 66 and 68, which both have an elongate opening 102, 104, respectively, and this permits a mobility of the friction plate 40 on the handle 18, according to the above description, in other words towards and away from the handle 18. The angles on the spring plates 66 and 68 provide for the corresponding pressing force and, consequently, for the firm locking between the control element 29 and the handle 18 on which the friction plate 40 is mounted.

The function of the bend control mechanism 30 will be explained in more detail with reference to FIG. 9 to FIG. 10a, and the fastening of the control wires 48 and 50 on the drum 46 will be described.

Figure 9:
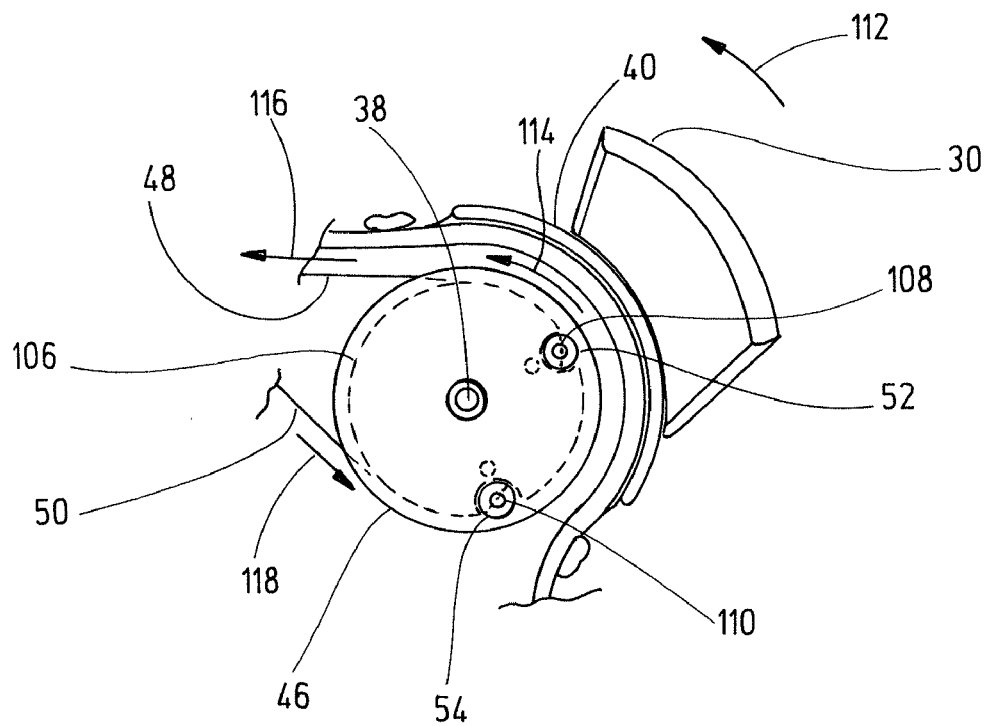
FIG. 9 shows a detail view as in FIG. 4, with control wires extending about a drum.
Figure 10:
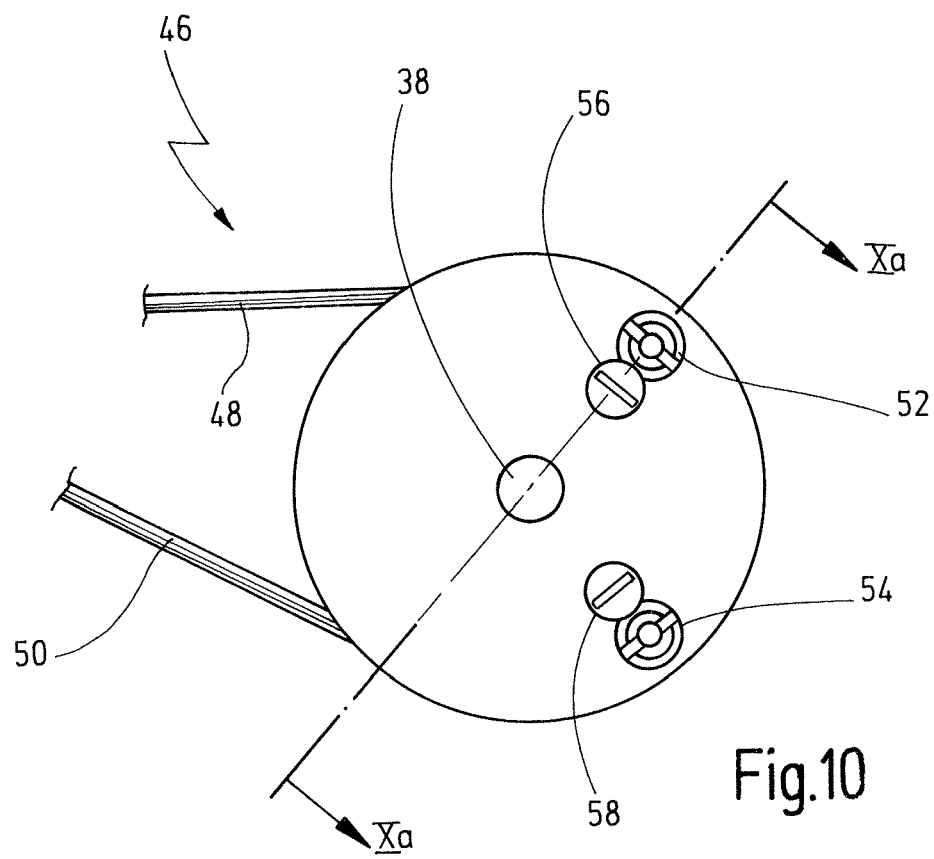
FIG. 10 shows a side view of the drum from FIG. 9.

FIG. 9 shows the course of the control wires 48 and 50 in the drum 46. The latter comprises a circumferential groove 106 in which the control wires 48 and 50 are guided, in order thereafter to end in bores 108 and 109 of the fastening screws 52 and 54. The control wires 48 and 50 are then mounted firmly on these.

If the control element 29 is now moved in the direction of the arrow 112, the drum 46, because of the above-described operative connection via the connecting arm 36, executes a rotation movement about the pivot axis 38, as is indicated by the direction of the arrow 114. For the control wires 48 and 50 secured on the drum 46, this means that they too execute a movement, specifically with the control wire 48 being pushed into the shaft 112 in the direction of the arrow 116 and with the control wire 50 being drawn out of the shaft in the direction of the arrow 118. As a result of the abovementioned operative connection of the control wires 48 and 50 to the bendable end 14, the angle setting of the latter is consequently changed. This results in a bending movement of the form represented by the bendable end 14' in FIG. 1.

The opposite movement again leads to a straightening of the shaft 12 or an upward bending movement as seen in FIG. 1. The setting or angle of the bendable end 14 can be locked in any desired position by releasing the trigger 72.

If the arrangement of the drum and of the control element were turned through 90°, this would result, not in the "up-down" bending plane shown in FIG. 1, but in a "left-right" bending plane turned 90° about the shaft axis. The control wires can also be arranged the other way round, in which case, for example, a "forward" displacement of the control element 29 leads to an "upward" bending movement instead of a "downward" bending movement.

Figure 10A:
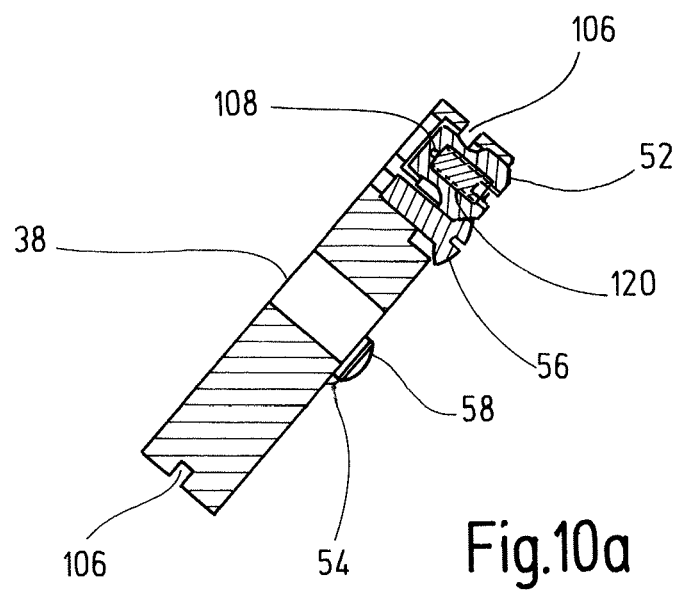
FIG. 10a shows a cross section along the line Xa-Xa in FIG. 10.

FIG. 10a shows the circumferential groove 106. It also shows the bore 108 of the fastening screw 52. Through this, in the example mentioned here, the control wire 48 is inserted into the fastening screw 52 and mounted firmly in this fastening screw by means of a fixing screw 120. The same applies to the fastening screw 54, not shown here in the cross section, and to the control wire 50. The length of the control wires 48 and 50 can then be adjusted by individual rotation of the screws 52 and 54. In one illustrative embodiment, these have mutually different threads for this purpose, such that fastening screw 52 has a right-hand thread and fastening screw 54 has a left-hand thread. After the control wires 48 and 50 have been adjusted, the fastening screws 52 and 54 are fixed by means of the securing screws 56 and 58. These prevent independent rotation of the fastening screws 52 and 54 and thus prevent unwanted adjustment of the control wires 48 and 50.

In FIGS. 11 to 16, the design and assembly of the insert 22 are described.

The insert 22 shown in FIG. 11 has at its distal end a tool 126, in this case two spreadable jaw parts 127, 127', which tool is operatively connected to a connection piece 130 via a rod-shaped flexible actuating element 128. Mounted proximally behind the tool 126, there are a hood 124 and a screw closure 122 which both serve to fasten the insert 22 on a flexible shaft, e.g. on the flexible shaft 12 from FIG. 1. As has already been mentioned, the proximal end of the insert 22 has the connection piece 130, which serves, for example, for fastening on the grip part 20 of the medical instrument 10. For this purpose, in this illustrative embodiment, the end has a spherical shape and is arranged proximally behind a portion 131 of smaller diameter on the insert 22.

FIG. 12 shows the fastening of the distal end of the insert 22 on the distal end of the shaft 12. The hood 124 located proximally behind the tool 126 is connected firmly to the insert 22. This prevents the screw closure 122 from slipping in a distal direction. This screw closure 122 is for its part then screwed onto an outer thread 123 at the distal end of the shaft 12. For this purpose, the force transmission element 128 is first inserted from the distal direction into the shaft 12. The distal end of the insert 22 is fixed in position by this fastening. A bending of the bendable end 14 then no longer causes the insert 22 to be pushed out from the distal end of the shaft 12.

FIGS. 13 to 16 show the grip part 20, the pivot axis 32 thereof and a catch 132 for releasable connection to the proximal end of the insert 22. FIG. 13a shows an opening 136 which opens in the direction of the pivot axis 32 and through which the spherical end of the connection piece 130 is inserted. The portion 131 of small diameter following distally from this on the insert 22 can be guided out laterally from the interior of the grip part 20 via a groove 138 (see FIG. 15). To introduce the end of the insert 22, a catch 132 has to be pressed such that the connection piece 130 can pass the latter. This can be seen from FIGS. 14 and 14a.

The catch 132 shown in FIG. 16 is held by a retainer 146 on the grip part 20. It is further pressed against the edge of this retainer 146 by a spring 148. The position shown in FIG. 14 thus represents the starting position of the catch 132. It will be seen how the connection piece 130, because of its spherical end here, is blocked by the catch 132 and therefore cannot pass upwards, with reference to the drawing, through the opening 136. If the catch 132 is now actuated counter to the direction in which it is pressed by the spring 148, that is to say in the direction of the arrow 147, a recess 144 which is provided on the catch 132, which is located to the right of the connection piece 130 in the view in FIG. 14, moves into a central position of the opening 136, as is shown by way of example in FIG. 14a. This pressing-in can be done via a knob 145 which protrudes laterally outwards past the retainer 146.

This recess 144 gives the spherical connection piece 130 enough room to move past this catch 132. In this way, the connection piece 130 can be removed from the retainer in the grip part 20 by way of the opening 136. When the catch 132 is released again, it moves back out again in the direction of the arrow 149 in FIG. 14a. The reason for this is once again the spring 148. At the same time, the recess 144 also moves then.

If the connection piece 130 is then to be fitted back into the retainer of the grip part 20, the catch 132 has to be pressed back in the direction of the arrow 147 in FIG. 14, such that the recess 144 comes to lie once more in the central position, as is shown in FIG. 14a. In this way, the spherical end can be guided past the catch 132 again, and the connection piece 130 can be fastened on the grip part 20 via the opening 136.

FIG. 15 shows how a connection piece 130 is located under the catch 132. An upward movement is not possible. The portion 131 of small diameter on the proximal end of the insert 22 fits through the groove 138, thus permitting mobility in the direction of the double arrow 151. This freedom of movement is needed in the movement of the grip part 20.

To avoid a rotation of the catch 132 pivotable about the longitudinal axis, and thus also to avoid a rotation of the recess 144, an axial groove 142 is formed at the distal end of the catch 132. This groove 142 also serves as an abutment for the displacement movement. This is shown in FIGS. 14 and 14a, and also in the perspective view in FIG. 16. A pin 140 now ends in this groove 142 upon fastening in the grip part 20 and, although it prevents undesired rotation about the longitudinal axis of the catch 132, it nevertheless permits an axial mobility of the catch 132 in the direction of the arrows 147 and 149.

In FIGS. 17 to 20, the lock connection formed by the lock 24 on the grip part 20 is shown in detail.

The lock 24 is mounted in a recess 163 on the handle 18 so as to be pivotable about a pivot axis 150. In this illustrative embodiment, this lock 24, by contact with the grip part 20, can suppress the movement of the grip part 20 in the distal direction. For this purpose, the lock 24 is pressed in the direction of the grip part 20 by the pretensioning afforded by a spring plate 166.

For this purpose, the lock 24, on its side directed towards the grip part 20, has locking teeth 174 which come into engagement with a locking pin 160 on the grip part 20. The inclination of the flanks of the locking teeth 174 in the direction of the handle 18 permits a movement of the grip part 20 in the direction of the handle 18, but block this in the opposite direction.

Figure 18:
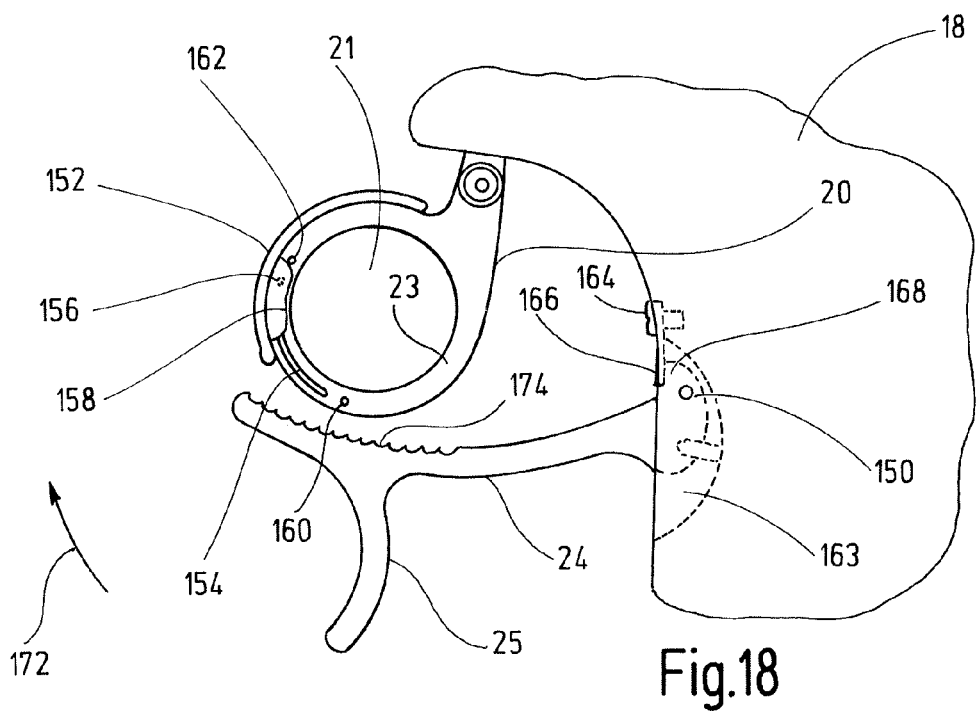
FIG. 18 shows a view corresponding to FIG. 17, with the lock connection released.

If the lock connection is to be released briefly, the lock 24 is pivoted in the direction of the arrow 170, preferably by actuation via the arc-shaped attachment 25, which leads to an end position as shown in FIG. 18. Because of the pretensioning, the lock 24, when released, is brought back again to the grip part 20 in the direction of the arrow 172.

In order to deactivate the lock connection for a period of time, a detent 152 is provided on the grip part 20.

The detent 152 is designed as a curved element, in the illustrative embodiment shown here as a curved strip 153 (see also FIG. 13a) whose curvature is adapted to the curvature of the outer face of the ring section 23 of the grip part 20.

Recesses or punches 155 in the strip 153 increase its grip.

Figure 17:
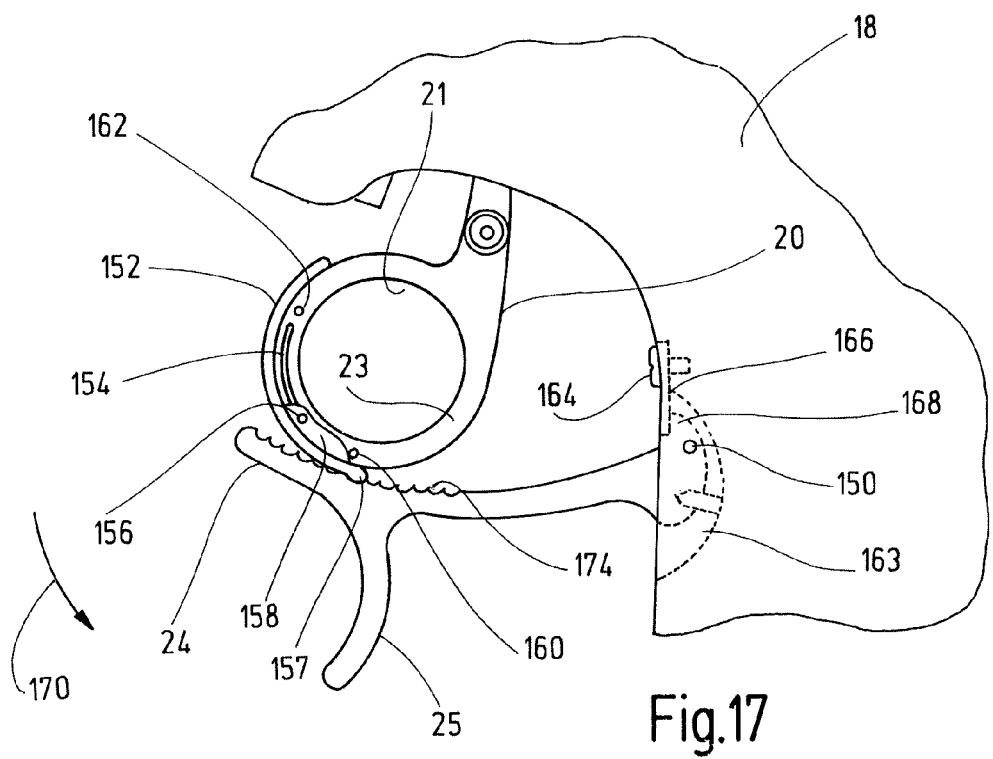
FIG. 17 shows a detail view of a medical instrument in the area of the grip part in order to illustrate the lock connection.

As can be seen in FIG. 17, this detent 152 can be brought between grip part 20 and lock 24. In this case, the lock connection is deactivated and the grip part 20 is movable freely in both directions. For this purpose, the detent 152 has a rounded nose 157, which can run in both directions over the teeth 174. This corresponds to a second position of the detent 152. In order now to reactivate the lock connection, the detent 152 can be pushed in the direction of a locking pin 162. This corresponds to a first position of the detent 152. A cover 158 is provided on both sides of the strip 153. This cover 158 conceals a guide pin 156 which extends transversely in the detent and which runs in guide grooves 154 on both sides of the ring section 23. The covers 158 themselves can be fastened on the detent 152 by pins (not shown here). Accordingly, the detent 152 extends through a circular movement, as is defined by the shape of the ring section 23 of the grip part 20, and thus ends in a position as shown in FIG. 18. In this way, a locking pin 160 previously blocked by the detent 152 now lies free and can come into engagement with the teeth 174 of the lock 24.

Figure 19:
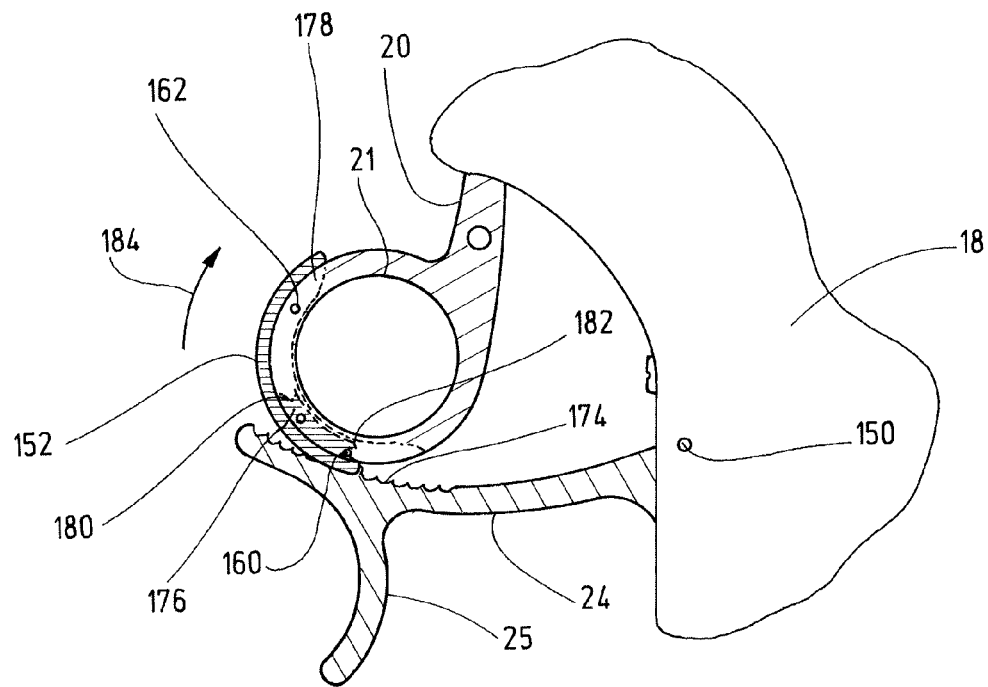
FIG. 19 shows a view corresponding to FIG. 17, as a cross section seen in the viewing plane and with the lock connection deactivated.
Figure 20:
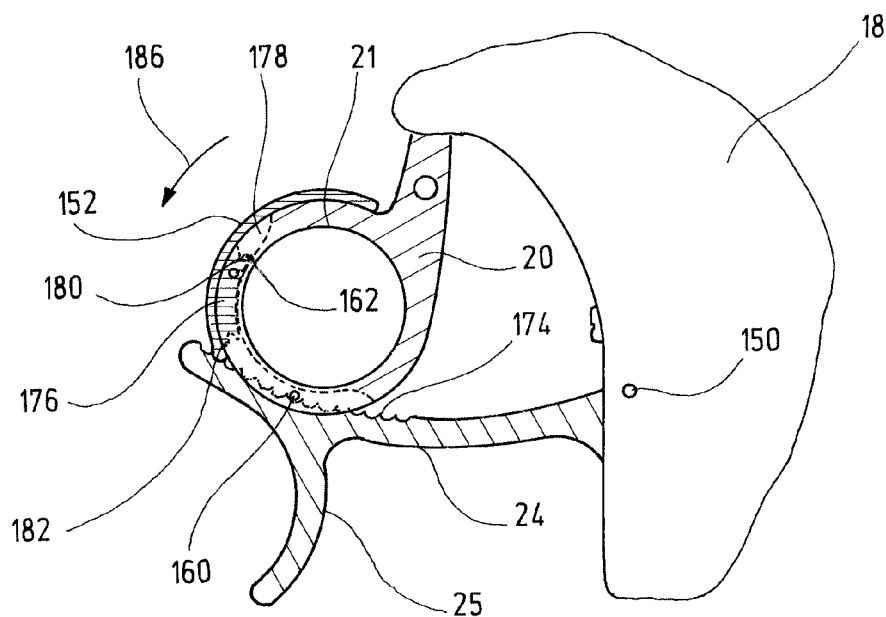
FIG. 20 shows a view corresponding to FIG. 19, with the lock connection activated.

As is shown in FIGS. 19 and 20, an outer groove 178 is cut into the circumference of the grip part 20. A step 176 of the detent 152 projecting in the radial direction of the ring section 23 can be moved in this groove 178, which step 176 is arranged centrally on the detent 152. Spring clips 180 and 182 are arranged respectively at each end of this step 176. They are able to engage in the locking pins 160 and 162, respectively, in accordance with the position of the detent 152 and thus prevent a simple reciprocating sliding of the detent 152. The latter is thus held in the respective positions.

FIG. 19 shows, in this connection, the second position of the detent 152, in which the lock connection is deactivated. The spring clip 182 of the step 176 on the detent 152 is engaged in the locking pin 160 and thus blocks the contact between the locking teeth 174 and the locking pin 160. A movement of the detent 152 in the direction of the arrow 184 would finally end in the first position, as is shown in FIG. 20. The spring clip 180 located on the step 176 is engaged in the locking pin 162, and the detent 152 is thus fixed in this position. The locking pin 160 thus lies free and is able to hook into the teeth 174 of the lock 24.

By contrast, a proximal movement of the grip part 20, which would lead for example to a closing of the jaw parts 127, 127', is again possible via the lock 24.

The lock connection can now be deactivated again by moving the detent 152 analogously to what has been stated above in the direction of the arrow 186, preferably after the lock 24 has been lowered, in accordance with the description of FIGS. 17 and 18.

As can be seen in FIG. 1a, the operator can hold the instrument 10 via the handle 18. The trigger 72 can be pressed by the thumb and the control element 29 then displaced. This causes a corresponding bending of the bendable end 14 of the shaft. Release of the trigger 72 stops the bendable end 14 in the corresponding position.

A movement of the grip part 20, e.g. by the inserted index finger, permits the opening and closing of the jaw parts 127, 127 via the insert 22 in any desired angled position of the bendable end 14 of the shaft 12.

When the lock function is deactivated, the movement of the grip part 20 is possible in both directions of pivoting.

When the lock function is activated, this can be quickly obtained by pivoting the lock 24 with the middle finger via the arc-shaped attachment 25.

The operator is thus able to manoeuvre the medical instrument 10 easily and safely and in a highly ergonomic manner.

What is claimed is:

1. A medical instrument comprising;
   a shaft,
   a handle connected to a proximal end of said shaft,
   an insert guided along said shaft, said insert being connected at a proximal end to a movable grip part of said handle, and having a tool at a distal end, said tool being actuated by said movable grip part, and
   a lock which can be brought into a locking engagement with said movable grip part, wherein
   a detent is provided, said detent can be brought between said lock and said movable grip part, thereby cancelling a lock function of said lock by said detent,
   wherein said detent can be brought from a first position, in which said lock function is unaffected to a second position, in which said lock function is cancelled,
   wherein clip elements are arranged on said detent and enter into connection with retaining pins when said detent is either in said first or said second position, and
   wherein in said second position, one of said clip elements enters into a retaining connection with said locking pin that engages with said lock.

2. The medical instrument of claim 1, wherein said detent can be held in said first position.

3. The medical instrument of claim 1, wherein said detent can be held in said second position.

4. The medical instrument of claim 1, wherein said detent is guided in a guide.

5. The medical instrument of claim 4, wherein said guide has at least one groove in which a projecting element of said detent engages.

6. The medical instrument of claim 1, wherein said detent is rounded in an area that comes into contact with teeth of said lock.

7. The medical instrument of claim 1, wherein said detent is mounted on said movable grip part.

8. The medical instrument of claim 7, wherein said detent is mounted displaceably on said grip part and can be displaced there between said first and said second positions.

9. The medical instrument of claim 7, wherein said movable grip part has a finger opening having a ring section, said detent is mounted on said ring section.

10. The medical instrument of claim 9, wherein said detent is designed as a curved element, whose curvature is adapted to said ring section of said grip part.

11. The medical instrument of claim 10, wherein said curved element has features increasing its grip.

12. The medical instrument of claim 11, wherein said features for increasing said grip of said curved element are selected from the group of elevations, flutings, recesses, punches, hollows.

13. The medical instrument of claim 9, wherein pins project from said detent and each pin engage a groove on sides of said ring section.

14. The medical instrument of claim 13, wherein said detent has lateral covers that engage laterally over said ring section of said movable grip part.

15. The medical instrument of claim 9, wherein said detent extends along an outer face of said ring section.

16. The medical instrument of claim 1, wherein said clip elements are arranged on a step extending in a circumferential groove that is cut out on said movable grip part.

17. The medical instrument of claim 1, wherein said lock is designed as a pivotable lever which is pretensioned in a direction of said movable grip part and which is articulated on said handle.

18. The medical instrument of claim 1, wherein said lock has an attachment via which said lock can be withdrawn from said movable grip part.

19. The medical instrument of claim 18, wherein said attachment is arch-shaped and can receive a finger of a hand that has taken hold of said handle.

* * * * *

UNITED STATES PATENT AND TRADEMARK OFFICE
Certificate

Patent No. 8,398,618 B2  Patented: March 19, 2013

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Uwe Bacher, Tuttlingen (DE); Sabine Zahler, Vaterstetten (DE); and Sebastian Frey, Waghaeusel (DE).

Signed and Sealed this Second Day of July 2013.

S. THOMAS HUGHES
*Supervisory Patent Examiner*
Art Unit 3731
Technology Center 3700